(12) United States Patent
Williams et al.

(10) Patent No.: US 12,311,314 B2
(45) Date of Patent: May 27, 2025

(54) SILOXANE REMOVAL SYSTEMS AND METHODS

(71) Applicant: GraniteFuel Engineering Inc., Concord (CA)

(72) Inventors: Shazam S. Williams, Toronto (CA); Linjie Hu, Vaughan (CA)

(73) Assignee: GRANITEFUEL ENGINEERING INC., Concord (CA)

( * ) Notice: Subject to any disclaimer, the term of this patent is extended or adjusted under 35 U.S.C. 154(b) by 390 days.

(21) Appl. No.: 17/795,593

(22) PCT Filed: Jan. 29, 2021

(86) PCT No.: PCT/CA2021/050101
§ 371 (c)(1),
(2) Date: Jul. 27, 2022

(87) PCT Pub. No.: WO2021/151206
PCT Pub. Date: Aug. 5, 2021

(65) Prior Publication Data
US 2023/0096898 A1    Mar. 30, 2023

Related U.S. Application Data (60) Provisional application No. 62/967,084, filed on Jan. 29, 2020.

(51) Int. Cl.
*B01D 53/75*     (2006.01)
*B01D 53/00*     (2006.01)
(Continued)

(52) U.S. Cl.
CPC .......... *B01D 53/75* (2013.01); *B01D 53/005* (2013.01); *B01D 53/1468* (2013.01);
(Continued)

(58) Field of Classification Search
None
See application file for complete search history.

(56) References Cited

U.S. PATENT DOCUMENTS

| 6,712,885 B1 | 3/2004 | Basseen et al. |
| 9,890,674 B2 | 2/2018 | Williams et al. |
| (Continued) | | |

FOREIGN PATENT DOCUMENTS

| EP | 1997549 B1 | 9/2010 |
| JP | 2014006221 A | 1/2014 |
| (Continued) | | |

OTHER PUBLICATIONS

Urban et al., "Catalytically upgraded landfill gas as a cost-effective alternative for fuel cells", Journal of Power Sources 193 (2009) pp. 359-366.
(Continued)

*Primary Examiner* — Jason M Greene
(74) *Attorney, Agent, or Firm* — Smart & Biggar LP (57) ABSTRACT

Systems for and methods of treating a fluid containing siloxanes, silanes and/or other silicon compounds. A hot box is configured to receive an initial flow of the fluid, react the flow with water at a temperature and pressure suitable for hydrolysis to generate a first treated flow, in which at least a portion is hydrolyzed to produce silicon dioxide and methane, and discharge the first treated flow. A solid removal mechanism can be configured to receive the first treated flow, separate at least a portion of the silicon dioxide as solid material, and discharge the remaining components as a second treated flow. Techniques of the present disclosure can lead to very low siloxane levels.

25 Claims, 6 Drawing Sheets

(51) Int. Cl.
  *B01D 53/14* (2006.01)
  *B01D 53/72* (2006.01)
  *C01B 33/113* (2006.01)
(52) U.S. Cl.
  CPC ............ *B01D 53/72* (2013.01); *C01B 33/113* (2013.01); *B01D 2253/102* (2013.01); *B01D 2253/104* (2013.01); *B01D 2253/106* (2013.01); *B01D 2253/116* (2013.01); *B01D 2255/808* (2013.01)

(56) References Cited

U.S. PATENT DOCUMENTS

| | | | |
|---|---|---|---|
| 10,843,118 B2 | 11/2020 | Muter et al. | |
| 2004/0045440 A1 | 3/2004 | Baseen et al. | |
| 2006/0225571 A1 | 10/2006 | Higgins | |
| 2007/0086931 A1* | 4/2007 | Raoux | B01D 53/75 422/177 |
| 2013/0034465 A1* | 2/2013 | Kanno | G01N 33/0014 422/51 |
| 2013/0209338 A1 | 8/2013 | Prasad et al. | |
| 2013/0346016 A1* | 12/2013 | Suzuki | A61B 5/1123 702/141 |
| 2015/0209717 A1 | 7/2015 | Ballantyne et al. | |
| 2016/0206990 A1 | 7/2016 | Bossan | |
| 2018/0163587 A1 | 6/2018 | Williams et al. | |

FOREIGN PATENT DOCUMENTS

| | | | | |
|---|---|---|---|---|
| JP | 2014-83551 | * | 5/2014 | ............ B01D 53/86 |
| JP | 201483511 A | | 5/2014 | |
| JP | 2014083511 A | | 5/2014 | |
| KR | 20170036561 A | | 4/2017 | |
| WO | 2018189027 A1 | | 10/2018 | |
| WO | 2021174349 A1 | | 9/2021 | |
| WO | 2022126278 A1 | | 6/2022 | |

OTHER PUBLICATIONS

International Search Report and Written Opinion dated Apr. 6, 2021 in respect of PCT/CA2021/050101.

Sonoc et al., "Kinetic study of the thermal decomposition of octamethylcyclotetrasiloxane on activated gamma alumina", Journal of Environmental Chemical Engineering 5 (2017) pp. 4858-4865.

Finocchio et al., "Decomposition of hexamethylcyclotrisiloxane over solid oxides", Chemosphere 72 (2008) pp. 1659-1663.

Davidson et al., "Kinetics of the Thermolysis of Octamethylcyclotetrasiloxane in the Gas Phase", Feb. 26, 2075, pp. 2260-2265.

Preißinger et al., Thermal Stability of Hexamethyldisiloxane (MM) for High-Temperature Organic Rankine Cycle (ORC), Energies 2016, 9, 183; doi: 10.3390.

Extended European Search Report dated Dec. 15, 2023 in respect of European Application No. 21748398.1.

Montanari et al., Purification of landfill biogases from siloxanes by adsorption: A study of silica and 13X zeolite adsorbents on hexamethylcyclotrisiloxane separation, Chemical Engineering Journal 165 (2010) 859-863.

* cited by examiner

SILOXANE REMOVAL SYSTEMS AND METHODS

CROSS REFERENCE TO RELATED APPLICATIONS

This is a national stage application of International Application No. PCT/CA2021/050101 filed on Jan. 29, 2021, which claims priority to U.S. Provisional Application No. 62/967,084 filed on Jan. 29, 2020, and the entire contents of each are hereby incorporated herein by reference.

FIELD

The present disclosure relates generally to fluid treatment to remove contaminants.

BACKGROUND

The following paragraphs are not an admission that anything discussed in them is prior art or part of the knowledge of persons skilled in the art.

Japanese Application No. 2014-83511 A discloses a siloxane decomposition apparatus for removing cyclic siloxane by hydrolysis reaction of cyclic siloxane and water vapor on a catalyst. The siloxane decomposition apparatus introduces a siloxane-containing gas into the siloxane decomposition catalyst from the outside of the apparatus through a gas inlet by being sucked by a suction blower. The gas supplied from the outside is heated by a gas preheater to the temperature required for the hydrolysis reaction to proceed to the temperature of the siloxane decomposition catalyst. Usually, the temperature of the catalyst layer is set in the range of 150 to 300° C., and water vapor is required for the hydrolysis reaction, so that it is supplied from the water supply device to the upstream position of the siloxane decomposition catalyst. Water vapor remaining without being consumed in the reaction is condensed by the cooler and recovered.

U.S. Pat. No. 9,890,674 B2 discloses a method of removing impurities from a gas including the steps of removing impurities from biogas comprising at least one adsorbents via a process vessel or reactor, directing the purified gas to an device to generate power and/or heat, regenerating the saturated adsorption media with the waste heat recovered from the engine exhaust and directing the regeneration gas (hot air or engine exhaust) to flare, engine exhaust stack, or atmosphere.

U.S. Pat. No. 10,843,118 discloses a filtration apparatus for filtering a fluid stream that includes a vessel housing. At least one cartridge assembly is arranged within the vessel housing. The cartridge assembly includes filtration material arranged between at least one inlet and at least one outlet. The filtration material treats the fluid stream to form a filtered fluid stream. In use, the fluid stream is received a feed port of the vessel housing, flows through the filtration material in the cartridge assembly between the inlet and the outlet, and the filtered fluid stream is discharged from a discharge port of the vessel housing. The filtration apparatus can be used to remove siloxanes from the fluid stream.

INTRODUCTION

The following is intended to introduce the reader to the detailed description that follows and not to define or limit the claimed subject matter.

In an aspect, the present disclosure relates to a system for treating a fluid containing siloxanes, silanes and/or other silicon compounds. The system can include: a hot box configured to receive an initial flow of the fluid, and react the initial flow with water at a temperature and pressure suitable for hydrolysis to generate a first treated flow. At least a portion of the initial flow is hydrolyzed to produce silicon dioxide and methane. At least a portion of the silicon dioxide is separated as a solid material, with the remaining components forming a second treated flow.

In an aspect, the present disclosure relates to a method of treating a fluid containing siloxanes, silanes and/or other silicon compounds. The method can include: providing an initial flow of the fluid; and reacting the initial flow with water at a temperature and pressure suitable for hydrolysis to generate a first treated flow. At least a portion of the initial flow is hydrolyzed to produce silicon dioxide and methane. At least a portion of the silicon dioxide is separated as solid material, with the remaining components forming a second treated flow.

In an aspect, the present disclosure relates to a system that can include: a hot box configured to receive an initial flow of a fluid containing siloxanes, silanes and/or other silicon compounds, react the initial flow with water at a temperature and pressure suitable for hydrolysis to produce silicon dioxide and methane; and adsorbent material housed in the hot box and configured to capture at least a portion of the silicon dioxide as solid material.

In an aspect, the present disclosure relates to a method that can include: providing an initial flow of a fluid containing siloxanes, silanes and/or other silicon compounds; reacting the initial flow with water at a temperature and pressure suitable for hydrolysis to produce silicon dioxide and methane; and capturing at least a portion of the silicon dioxide as solid material.

Other aspects and features of the teachings disclosed herein will become apparent, to those ordinarily skilled in the art, upon review of the following description of the specific examples of the present disclosure.

BRIEF DESCRIPTION OF THE DRAWINGS

The drawings included herewith are for illustrating various examples of apparatuses and methods of the present disclosure and are not intended to limit the scope of what is taught in any way. In the drawings.

DETAILED DESCRIPTION

Various apparatuses or methods will be described below to provide an example of an embodiment of each claimed invention. No embodiment described below limits any claimed invention and any claimed invention may cover apparatuses and methods that differ from those described below. The claimed inventions are not limited to apparatuses and methods having all of the features of any one apparatus or method described below, or to features common to multiple or all of the apparatuses or methods described below. It is possible that an apparatus or method described below is not an embodiment of any claimed invention. Any invention disclosed in an apparatus or method described below that is not claimed in this document may be the subject matter of another protective instrument, for example, a continuing patent application, and the applicant(s), inventor(s) and/or owner(s) do not intend to abandon, disclaim or dedicate to the public any such invention by its disclosure in this document.

Figure 1:
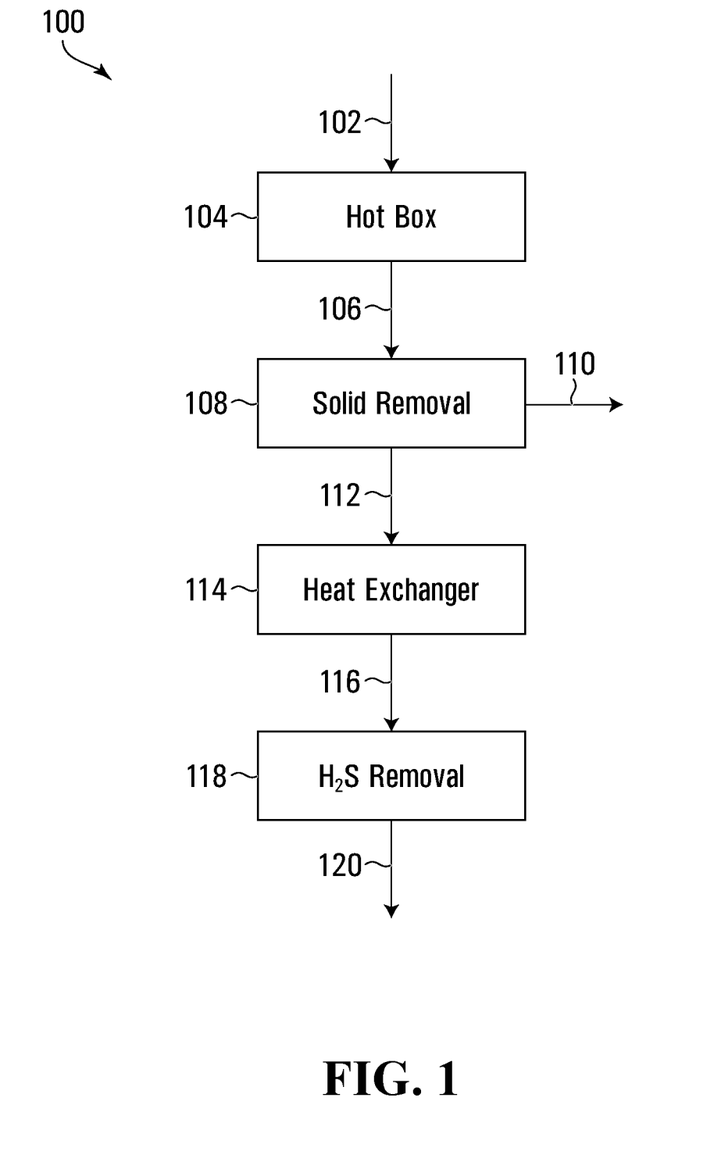
FIG. 1 is a schematic diagram of a first exemplary system.

Referring to FIG. 1, a system for treating a fluid containing siloxanes, silanes and/or other silicon compounds according to a first concept of the present disclosure is indicated generally at reference numeral 100. In the system 100, an initial flow 102 of the fluid to be treated is received at a hot box 104. The hot box 104 reacts the flow with water at a temperature and pressure suitable for hydrolysis, in which the siloxane reacts with water and is hydrolyzed and decomposes to produce silicon dioxide and methane, to generate a first treated flow 106 that is discharged from the hot box 104. The first treated flow 106 can consist primarily of $SiO_2$, $CH_4$, $H_2S$, ash and other chemical components.

In some examples, the initial flow 102 can consist of raw biogas. In some examples, the fluid can comprise hydrogen sulfide, organic sulphur molecules, water, oxygen and/or organometallic compounds, including volatile organic compounds (VOCs). In some examples, prior to introduction to the hot box 104, the initial flow 102 can be pretreated, e.g., to remove hydrogen sulfide, oxygen and/or liquid water.

In some examples, the hot box 104 can be operated at a temperature between 100 to 800° C., or between 300 to 500° C. In some examples, the hot box 104 can be operated at approximately 500° C. to hydrolyze siloxane molecules. Gas pressure within the hot box 104 can vary, but practically pressure can be less than 2 bar.

In some examples, the hot box 104 can include catalytic materials and/or reactive adsorbent materials. Catalytic materials can be used to increase the rate of the hydrolysis reaction within the hot box. Adsorbent materials can be used to capture solid silicon dioxide in the hot box. In some examples, both catalytic and absorbent materials can be included, and/or one material that is both catalytic and absorbent. In some examples, the hot box 104 can exclude catalytic materials or adsorbent materials, in order to avoid silica deposition.

In the system 100, a solid removal mechanism 108 receives the first treated flow 106 from the hot box 104, and separates the silicon dioxide as solid material 110. The solid material 110 can consist primarily of $SiO_2$ and other ash components. The remaining components can then be discharged from the solid removal mechanism 108 as a second treated flow 112. The second treated flow 112 can consist primarily of $CH_4$, $CO_2$, $H_2S$, some $H_2O$ and other chemical components.

In some examples, the solid removal mechanism 108 can include a filter apparatus, a cyclone apparatus, an electrostatic precipitator apparatus, a thermophoretic deposition apparatus, and/or utilize another suitable separation technique.

In some examples, the solid removal mechanism 108 can be optional and omitted. In such examples, the solid silicon dioxide material can be deposited onto and captured by catalytic and adsorbent material housed within the hot box 104. The material can be, for example and not intended to be limiting, activated alumina, silica gel, molecular sieve 3A, molecular sieve 13X, and/or activated carbon. In such examples, the material can catalyze the hydrolysis reaction, and then the silicon reacts with the material, in effect poisoning the surface of the material in the hot box. The material can be replaced in the hot box periodically after significant buildup of the solid silicon dioxide.

With continued reference to FIG. 1, in the system 100, a heat exchanger 114 receives the second treated flow 112 from the solid removal mechanism 108, and can decrease its temperature to less than 150° C., to generate a cooled second treated flow 116. In some examples, the heat exchanger 114 can be a single heat exchanger or a number of heat exchangers designed to recover heat in the system by gas to gas or gas to liquid heat exchangers. The cooled second treated flow 116 can then be discharged from the heat exchanger 114.

Optionally, as illustrated, the system 100 can include a hydrogen sulfide removal mechanism 118 that receives the flow 116 and removes hydrogen sulfide therefrom, to generate a treated flow 120. In some examples, mechanism 118 can include removal media, e.g., activated carbon, iron sponge, iron supported on clay, or other materials with affinity towards removing $H_2S$. The treated flow 120 can consist of $CH_4$ and trace $H_2O$, which can then be discharged from the system 100 and used as process gas.

In some examples, it can be beneficial to arrange the optional hydrogen sulfide removal mechanism upstream of the hot box. In some examples, hydrogen sulfide scrubbing systems can require ~100% humidity, and therefore there can be sufficient water in the initial flow to the hot box such that additional water does not need to be injected. Secondly, hydrogen sulfide scrubbing can generate some moisture, i.e. $H_2S+FeO_x \rightarrow H_2O+FeS_x$, which can be used for hydrolysis in the hotbox. Furthermore, hydrogen sulfide removal can protect the downstream equipment.

Figure 2:
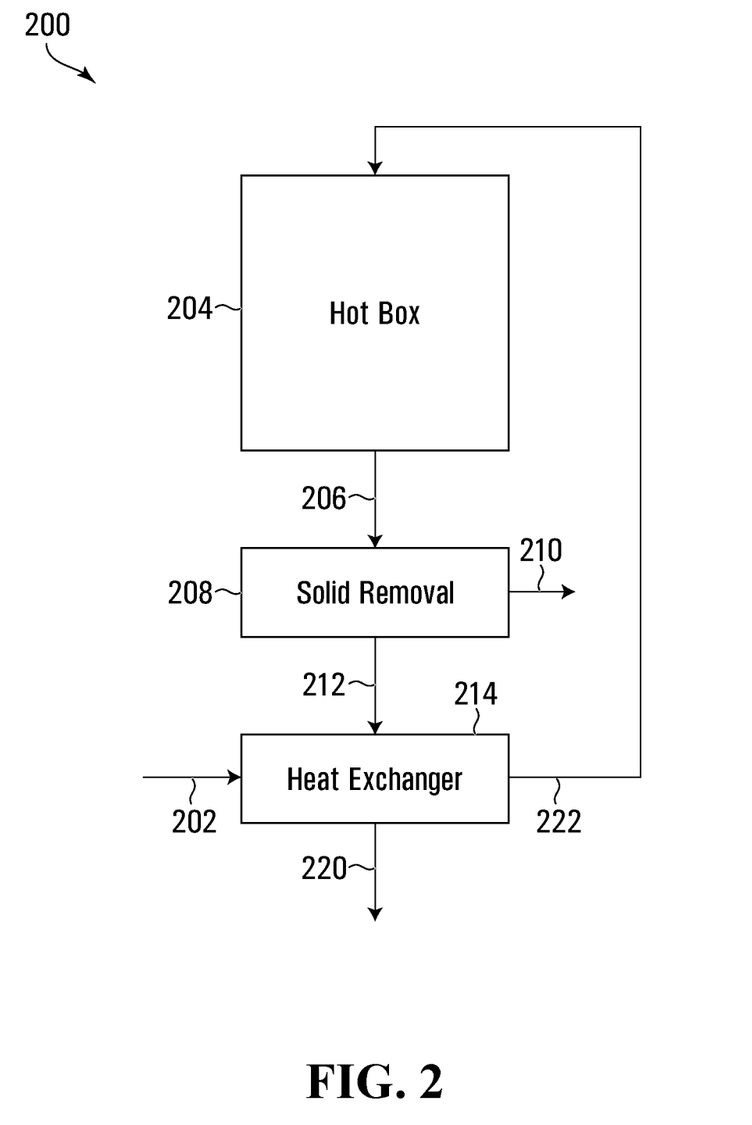
FIG. 2 is a schematic diagram of a second exemplary system.

Referring to FIG. 2, a system for treating a fluid containing siloxanes, silanes and/or other silicon compounds according to a second concept of the present disclosure is indicated generally at reference numeral 200. The system 200 is similar to the system 100. However, a heat exchanger 214 receives an initial flow 202 to increase its temperature, to generate a pre-heated flow 222. The heat exchanger 214 can be a single heat exchanger or a number of heat exchangers designed to recover heat in the system by gas to gas or gas to liquid heat exchangers.

In the example illustrated, the pre-heated flow 222 is then received at a hot box 204. The hot box 204 reacts the flow with water at a temperature and pressure suitable for hydrolysis, in which the siloxane reacts with the water and is hydrolyzed and decomposes to produce silicon dioxide and methane, to generate a first treated flow 206 that is discharged from the hot box 204.

In the example illustrated, a solid removal mechanism 208 receives the first treated flow 206 from the hot box 204, and separates the silicon dioxide as solid material 210. The remaining components can then be discharged from the solid removal mechanism 208 as a second treated flow 212.

In the example illustrated, the heat exchanger 214 receives the second treated flow 212 from the solid removal mechanism 208, and can decrease its temperature to generate a cooled treated flow 220. The flow 220 can then be discharged from the system 200 and used as process gas.

Figure 3A:
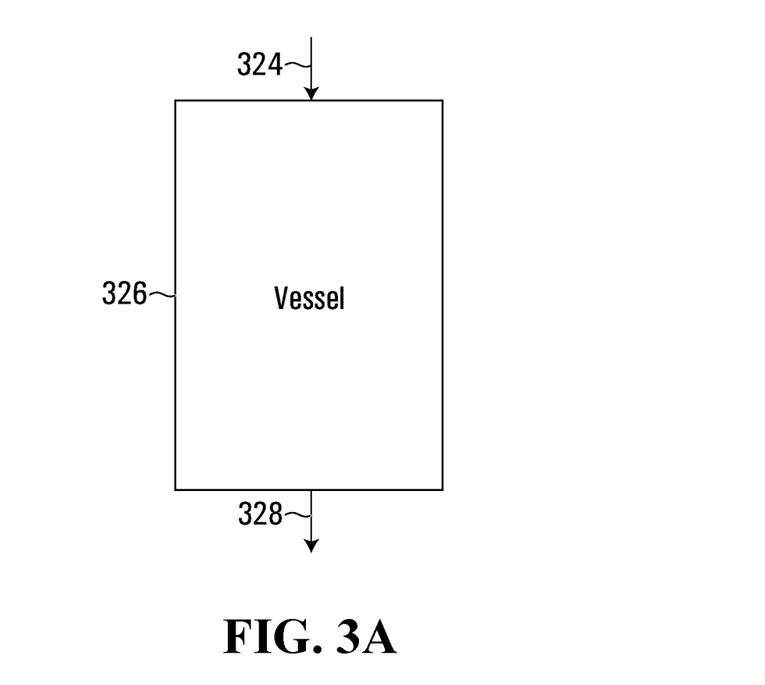
FIG. 3A is a schematic diagram of a siloxane treatment vessel.

Referring to FIG. 3A, a flow 324 of fluid to be treated is shown received by a siloxane treatment vessel 326. The vessel 326 can contain adsorbent media for capturing siloxane. The vessel 326 can remove siloxane from the flow 324, and discharge a treated flow 328. In some examples, the vessel can take the form of an apparatus disclosed in U.S. Pat. No. 10,843,118, the entire contents of which are hereby incorporated herein by reference.

Figure 3B:
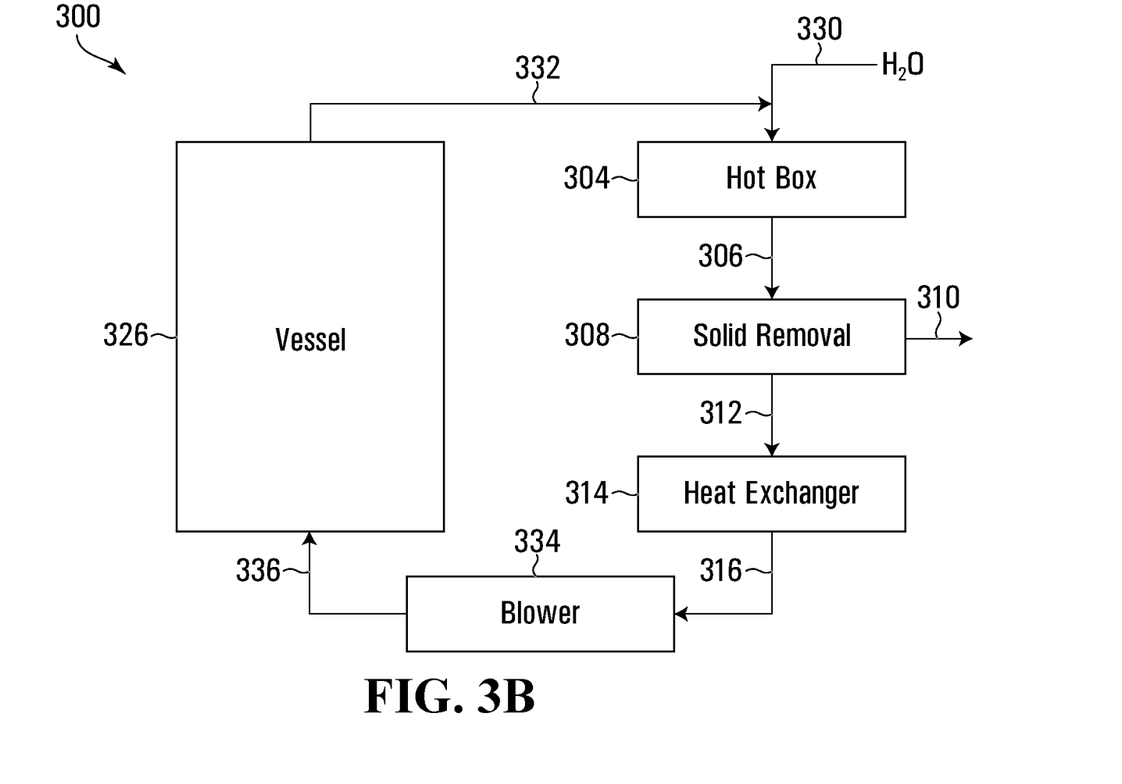
FIG. 3B is a schematic diagram of a third exemplary system including the siloxane treatment vessel.

Referring to FIG. 3B, a system for treating a fluid containing siloxanes, silanes and/or other silicon compounds according to a third concept of the present disclosure is indicated generally at reference numeral 300. The system 300 is similar to the systems 100, 200. However, the system 300 includes the vessel 326, and can be operated in accordance with a regeneration mode.

In the example illustrated, a water supply 330 can be combined with a flow 332 from the vessel 326 and received at a hot box 304. The hot box 304 reacts the flow with water at a temperature and pressure suitable for hydrolysis, in which the siloxane reacts with the water and is hydrolyzed and decomposes to produce silicon dioxide and methane, to generate a first treated flow 306 that is discharged from the hot box 304.

In the example illustrated, a solid removal mechanism 308 receives the first treated flow 306 from the hot box 304, and separates the silicon dioxide as solid material 310. The remaining components can then be discharged from the solid removal mechanism 308 as a second treated flow 312.

In the example illustrated, the heat exchanger 314 receives the second treated flow 312 from the solid removal mechanism 308, and can decrease its temperature to generate a cooled treated flow 316. In some examples, the heat exchanger 314 is needed to prevent siloxane media in the vessel 326 from being damaged by hot gas.

The system 300 is shown to include a blower 334 that draws the flow 316 from the heat exchanger 314 and delivers a flow 336 to the vessel 326. The blower 334 can be operated to control a circulation rate within the system 300, which can vary, e.g., 5-10 scfm.

Accordingly, the vessel 326 can be regenerated by sending the heated gas 336 into the siloxane-ladened vessel. In some examples, the water supply 330 can be controlled so that water is injected to the hot box 304 below a stoichiometric quantity for the siloxane hydrolysis reaction. This can be done to prevent hot steam from contacting the siloxane media in the vessel 326, which in some examples can be deactivated by steam.

The present disclosure relates generally to the removal of siloxanes and/or other silicon compounds from a fluid stream while reducing or avoiding the emission of waste gases to the environment. In some examples, the siloxanes can include low molecule weight organosilicon compounds, e.g., trimethylsilanol (TMS) and/or linear (L2) siloxane. The cleaned gas can be used subsequently in combustion processes, as a renewable natural gas (RNG), to operate fuel cells, etc.

In some examples, the approach is to thermally hydrolyze the siloxane with water. For example:

$$[(CH_3)_2SiO]_4 + 4H_2O = 4SiO_2 + 8CH_4$$

In some examples, solid $SiO_2$ particles can then be collected on an appropriate filter or other means and disposed in a landfill.

In some examples, as a side reaction, the approach can remove a portion of organic compounds, including VOCs, in the initial flow by a steam reforming reaction, i.e.:

Other side reactions can occur. In some examples, some organic sulfur compounds can react with water to produce hydrogen sulfide and organic compounds. In some examples, organic heavy metals and metalloids can be hydrolyzed or decomposed to corresponding metal oxides.

In some examples, techniques of the present disclosure can lead to very low siloxane levels, e.g., in the parts per billion (ppb) levels. In contrast, current techniques, such as deep chilling or adsorption systems, can be dependent on the vapor pressure of the component. For example, deep chilling to −20° C. can result in a treated gas with ~20 ppm of siloxanes.

In the following paragraphs, test procedures are described, which are intended to be illustrative but non-limiting.

A model gas reactor (MGR) system was used to conduct thermal hydrolysis experiments. The carrier gas was nitrogen gas from a bulk liquid nitrogen tank with high purity (99.999%). The carrier gas was flowed through a bubbler containing a siloxane compound and water at about 25° C., with a flow rate of 0.2~1.0 L/min. Various representative siloxane compounds in biogases were investigated, including octamethylcyclotetrasiloxane (D4), hexamethyldisiloxane (L2) and hexamethylcyclotrisiloxane (D3). The siloxane concentrations are provided in Table 1.

TABLE 1

| Feed gas composition during hydrolysis tests | | | |
|---|---|---|---|
| Siloxane component | D4 | L2 | D3 |
| Siloxane | 1200 ppm | 2200 ppm | 1200 ppm |
| $H_2O$ | 3% | 3% | 3% |
| $N_2$ | balance | balance | balance |

Figure 4:
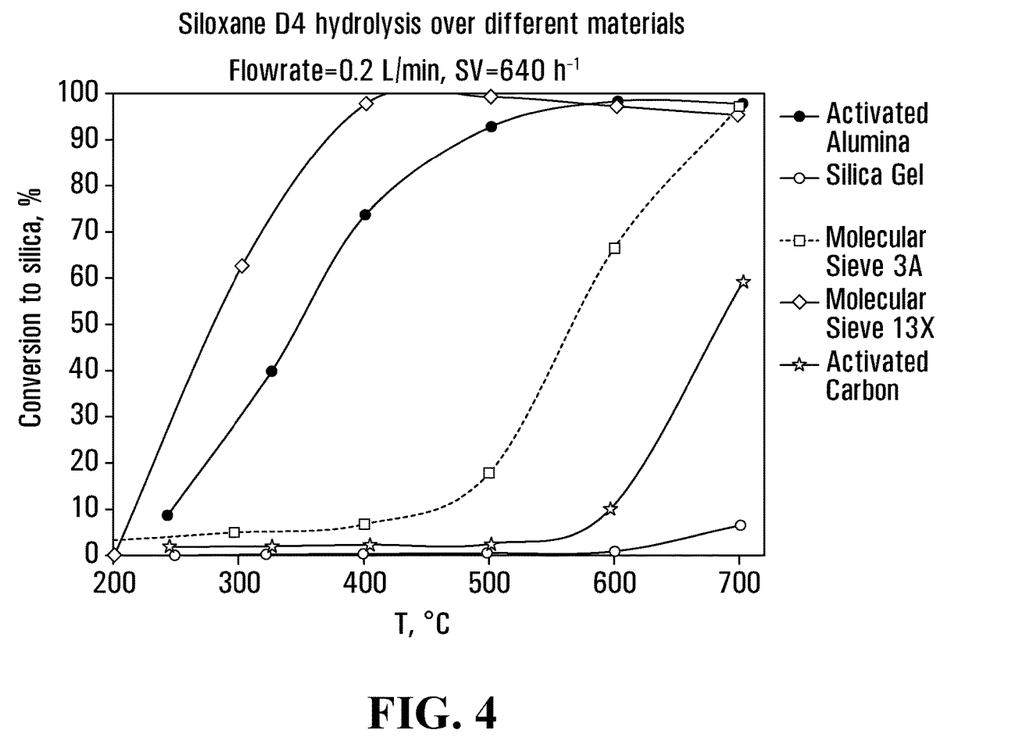
FIG. 4 is a graph showing siloxane hydrolysis over different materials.

Referring to FIG. 4, performance of different catalytic and adsorbent materials in the tests is shown. The exemplary materials are identified in Table 2. The molecular sieve 13X and activated alumina materials exhibited good performance. The molecular sieve 3A material started to exhibit some hydrolysis activity at about 200° C. However, the activated carbon and silica gel materials did not show activity towards siloxane hydrolysis until the reaction temperature reached about 600° C.

TABLE 2

| Adsorbent materials | | |
|---|---|---|
| Adsorbents | Brand name | Supplier |
| Activated Alumina | Activated Alumina F. 200 3/16" | Delta Adsorbents Division |
| Silica Gel | Silica Gel Granular 2-5 mm | Delta Adsorbents Division |
| Molecular Sieve 3A | Molecular Sieve 3A 1.6-2.5 mm | Jalon |
| Molecular Sieve 13X | Molecular Sieve 13X 1.6-2.5 mm | Jalon |
| Activated Carbon | Granular Activated Carbon MSC-3K-172 | Osaka Gas Chemicals Co., Ltd. |

With the molecular sieve 13X or activated alumina materials, the thermal hydrolysis reaction can take place at lower temperature than the other studied materials, at around 200° C. At about 400° C., the siloxane D4 conversion to silica can reach around 100% with the molecular sieve 13X, and around 75% with the activated alumina. The performance for D4 thermal hydrolysis was as follows:

13X>activated alumina>3A>activated carbon>silica gel

Figure 5:
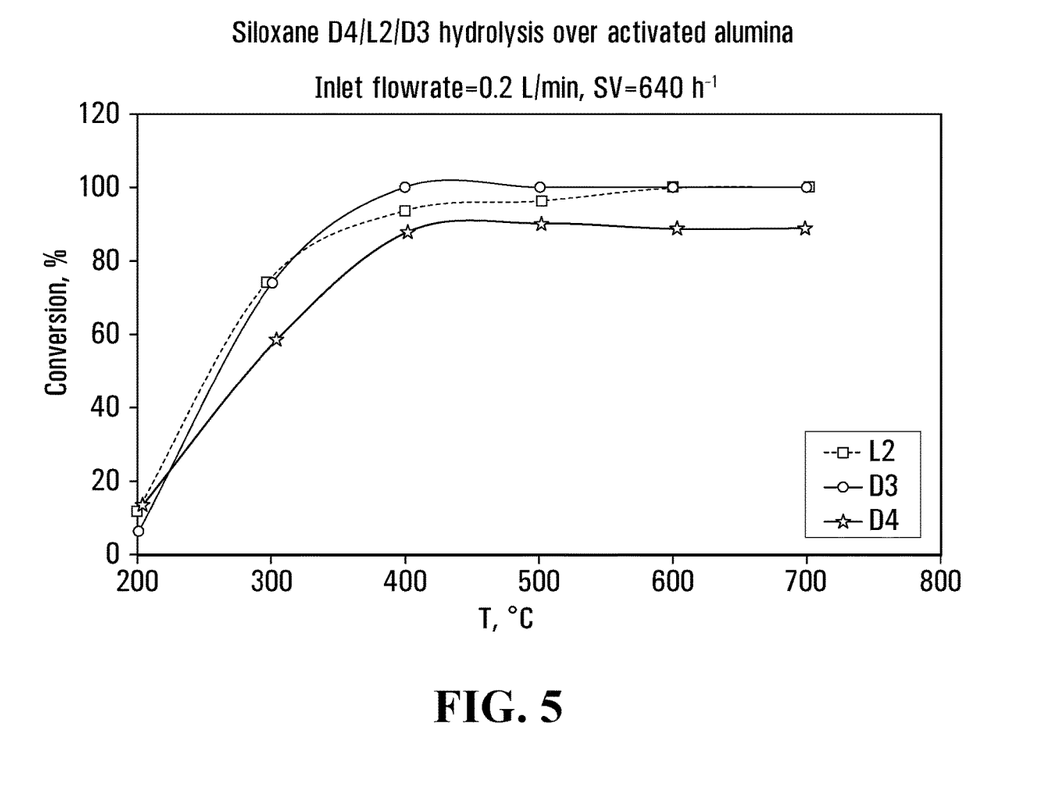
FIG. 5 is a graph showing siloxane hydrolysis over activated alumina.

In addition to D4, other siloxane species can be present in landfill or wastewater treatment plant biogases, such as L2 and D3. The hydrolysis of these representative siloxane species was conducted over activated alumina at a space velocity of about 640 h$^{-1}$. FIG. 5 demonstrates that these siloxane components can be hydrolyzed at about 400° C. or higher, with a similar activity pattern to D4. These thermal hydrolysis reactions over activated alumina can take place at about 200° C., and the conversion can reach 90-100% at about 400° C.

Figure 6:
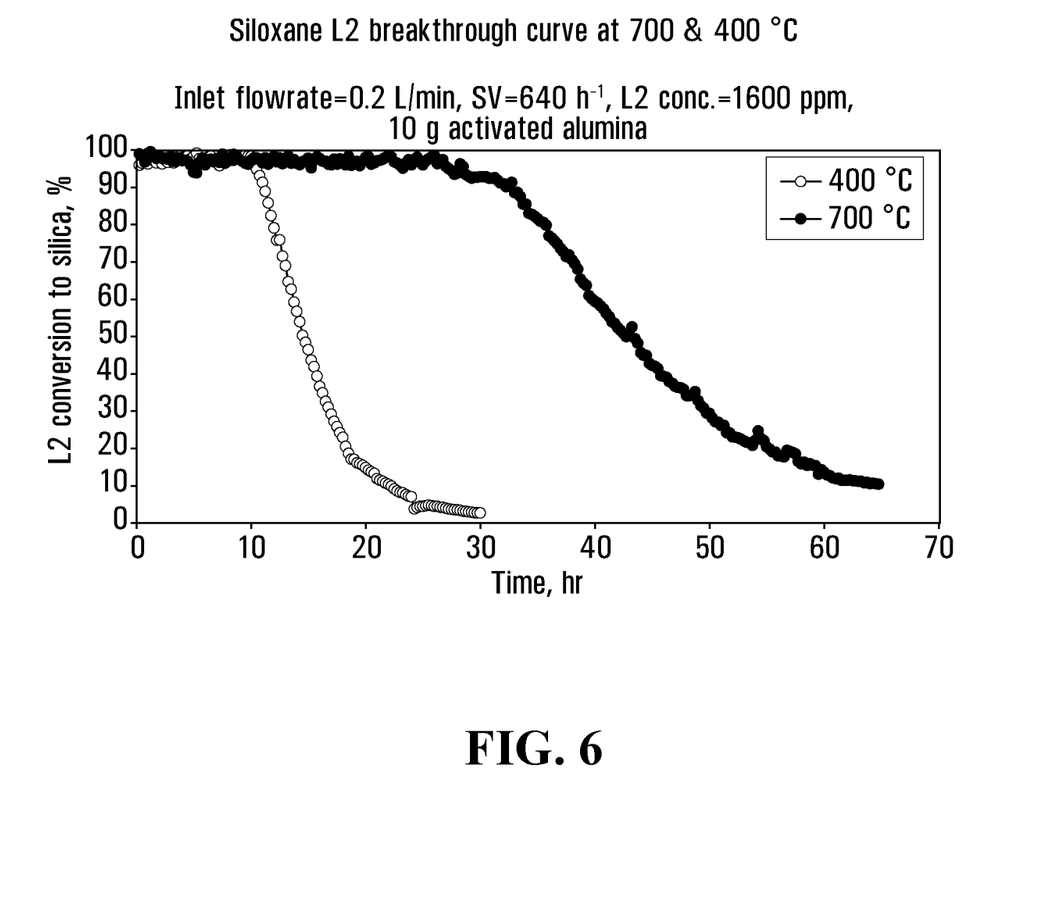
FIG. 6 is a graph showing siloxane breakthrough.

During the hydrolysis reaction, the product silicon dioxide can slowly deactivate the surface of activated alumina and the siloxane molecules can escape from the media bed. FIG. 6 shows the L2 breakthrough curve during hydrolysis reaction over activated alumina at 700 or 400° C. At 700° C., L2 conversion to silica is stable at around 100% for up to 25 hours. At 400° C., L2 conversion to silica is stable at around 100% for around 10 hours.

The capture capacity can be calculated based on the mass balance of the breakthrough curve. The elemental analysis results were consistent with the mass balance analysis. As shown in Table 3, the siloxane capacity is 202 mg/g media at 400° C., and 648 mg/g media at 700° C.

TABLE 3

Siloxane capacity of activated alumina, as L2

| Reaction temperature | Fresh media | Weight Gain | L2 capacity mg/g media |
| --- | --- | --- | --- |
| 400° C. | 10 g | 15% | 202 |
| 700° C. | 10 g | 48% | 648 |

While the above description provides examples of one or more apparatuses or methods, it will be appreciated that other apparatuses or methods may be within the scope of the accompanying claims.

We claim:

1. A system for treating a fluid containing siloxanes, silanes and/or other silicon compounds, comprising:
a hot box configured to receive an initial flow of the fluid, and react the initial flow with water at a temperature and pressure suitable for hydrolysis to generate a first treated flow,
wherein at least a portion of the initial flow is hydrolyzed to produce silicon dioxide and methane, and
wherein at least a portion of the silicon dioxide is separated as a solid material, with the remaining components forming a second treated flow; and
a vessel configured to receive the second treated flow, further remove siloxane, and discharge a third treated flow, and wherein, in a regeneration mode, the hot box is configured to receive the third treated flow as the initial flow.

2. The system of claim 1, wherein the hot box is operated at a temperature between 300 to 500° C.

3. The system of claim 1, wherein the hot box comprises catalytic material.

4. The system of claim 1, wherein the hot box comprises adsorbent material for capturing the silicon dioxide as the solid material.

5. The system of claim 4, wherein the adsorbent material is selected from at least one of activated alumina, silica gel, molecular sieve 3A, molecular sieve 13X, and activated carbon.

6. The system of claim 4, wherein the adsorbent material comprises activated alumina.

7. The system of claim 1, comprising a water supply for injecting water to the hot box.

8. The system of claim 1, comprising a solid removal mechanism configured to receive the first treated flow from the hot box, separate the portion of the silicon dioxide as the solid material, and discharge the remaining components as the second treated flow, wherein the solid removal mechanism comprises at least one of a filter apparatus, a cyclone apparatus, an electrostatic precipitator apparatus, and a thermophoretic deposition apparatus.

9. The system of claim 1, comprising at least one heat exchanger configured to receive the second treated flow, and decrease its temperature to less than 150° C., wherein the at least one heat exchanger is configured to receive the initial flow to increase its temperature before being received by the hot box.

10. The system of claim 1, comprising a hydrogen sulfide removal mechanism configured to remove hydrogen sulfide from the second treated flow.

11. The system of claim 1, comprising a blower configured to deliver the second treated flow to the vessel.

12. A method of treating a fluid containing siloxanes, silanes and/or other silicon compounds, comprising:
providing an initial flow of the fluid;
reacting the initial flow with water at a temperature and pressure suitable for hydrolysis to generate a first treated flow,
wherein at least a portion of the initial flow is hydrolyzed to produce silicon dioxide and methane, and
wherein at least a portion of the silicon dioxide is separated as a solid material, with the remaining components forming a second treated flow;
treating the second treated flow in a vessel to further remove siloxane, and discharging a third treated flow; and
in a regeneration mode, delivering the third treated flow as the initial flow for the steps of reacting and separating.

13. The method of claim 12, comprising, in the step of reacting, operating at a temperature between 300 to 500° C.

14. The method of claim 12, comprising, in the step of reacting, contacting the initial flow with catalytic material.

15. The method of claim 12, comprising, in the step of reacting, contacting the initial flow with adsorbent material to capture the silicon dioxide as the solid material.

16. The method of claim 15, wherein the adsorbent material is selected from at least one of activated alumina, silica gel, molecular sieve 3A, molecular sieve 13X, and activated carbon.

17. The method of claim 15, wherein the adsorbent material comprises activated alumina.

18. The method of claim 12, comprising:
in the step of reacting, injecting water; and
maintaining a concentration of the water below a stoichiometric quantity for the hydrolysis reaction.

19. The method of claim 12, comprising:
receiving the first treated flow, separating the portion of the silicon dioxide as the solid material, and discharging the second treated flow; and
in the step of separating, operating at least one of a filter apparatus, a cyclone apparatus, an electrostatic precipitator apparatus, and a thermophoretic deposition apparatus.

20. The method of claim 12, comprising decreasing a temperature of the second treated flow to less than 150° C.

21. The method of claim 20, comprising:
passing the second treated flow through at least one heat exchanger; and
before the step of reacting, passing the initial flow through the at least one heat exchanger to increase its temperature.

22. The method of claim 12, comprising at least partially removing hydrogen sulfide from the second treated flow.

23. The method of claim 12, comprising operating a blower to deliver the second treated flow to the vessel.

24. The method of claim 12, wherein the fluid consists of biogas.

25. The method of claim 12, wherein the fluid comprises hydrogen sulfide, organic sulphur molecules, water and organometallic compounds.

* * * * *